United States Patent [19]

Pinkos et al.

[11] Patent Number: 5,945,571
[45] Date of Patent: *Aug. 31, 1999

[54] PREPARATION OF 1,4-BUTANEDIOL

[75] Inventors: Rolf Pinkos, Bad Dürkheim; Rolf Fischer, Heidelberg; Boris Breitscheidel, Fulda; Peter Polanek, Weinheim, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,577

[22] PCT Filed: Jun. 16, 1995

[86] PCT No.: PCT/EP95/02335

§ 371 Date: Dec. 27, 1996

§ 102(e) Date: Dec. 27, 1996

[87] PCT Pub. No.: WO96/00203

PCT Pub. Date: Jan. 4, 1996

[30] Foreign Application Priority Data

Jun. 27, 1994 [DE] Germany ................ 4422051

[51] Int. Cl.⁶ .................................................. C07L 27/00
[52] U.S. Cl. ............................................................ 568/865
[58] Field of Search ..................... 568/861, 852, 568/865; 502/325, 330, 332

[56] References Cited

U.S. PATENT DOCUMENTS 4,476,332  10/1984  Nalepa .
4,859,801  8/1989  Ernst .

FOREIGN PATENT DOCUMENTS 340 170     11/1989  European Pat. Off. .
92/20667    11/1992  WIPO .
95/04023    2/1995   WIPO .
96/00203    1/1996   WIPO .

OTHER PUBLICATIONS

Fakely et al., Hydrogenation and Hydrogenation catalysts, Solid Supports and Catalysts in Organic Synthesis, pp. 275–287., 1992.

Primary Examiner—Michael L. Shippen
Attorney, Agent, or Firm—Keil & Weinkauf

[57] ABSTRACT

Described is a method of producing 1,4-butanediol, the method calling for 2,3-dihydrofuran to be decomposed in a single stage over a hydrogenation catalyst in the presence of water and hydrogen at a temperature of 20 to 300° C. and a pressure of 1 to 300 bar and in neutral or acid conditions.

11 Claims, No Drawings

PREPARATION OF 1,4-BUTANEDIOL

The present invention relates to a process for the preparation of 1,4-butanediol.

WO 92/20667 relates to a process for the preparation of 4-hydroxybutyraldehyde/2-hydroxytetrahydrofuran mixtures, in which, in a first stage, 2,5-dihydrofuran is isomerized to 2,3-dihydrofuran in the presence of rhodium-phosphine or ruthenium-phosphine complexes homogeneously dissolved in the reaction medium and is then removed, by distillation, from the reaction mixture. The 2,3-dihydrofuran is then caused to react with water over an acid catalyst to form a mixture of 4-hydroxybutanal and 2-hydroxytetrahydrofuran, and this mixture is isolated. The proposal made is to convert the mixture thus obtained to 1,4-butanediol by hydrogenation. Starting from 2,3-dihydrofuran, 2 stages are thus required in order to arrive at 1,4-butanediol.

U.S. Pat. No. 4,859,801 teaches that it is possible to cause reaction of 2,3-dihydrofuran with an aldehyde and hydrogen in the presence of water at a pH of from 8 to 14 using a hydrogenating catalyst to form mixtures of 1,4-butanediol and 2-alkyl-1,4-butanediol. The yield of 1,4-butanediol is moderate in this process. If the 2,3-dihydrofuran used in the reaction is hydrogenated directly, tetrahydrofuran is formed therefrom as main product. 1,4-Butanediol is formed in small amounts only.

EP-A 340,170 relates to the hydrogenation of 4-hydroxybutyraldehyde/2-hydroxytetrahydrofuran mixtures previously prepared in a separate procedure in a basic medium and in the presence of an aldehyde to form 2-alkyl-1,4-butanediols, part of this mixture being hydrogenated to 1,4-butanediol.

It was thus the object of the present invention to provide a process for the preparation of 1,4-butanediol starting from 2,3-dihydrofuran, which makes it possible to obtain 1,4-butanediol in a single stage in good yield and selectivity.

Accordingly, we have found a process for the preparation of 1,4-butanediol, wherein 2,3-dihydrofuran is caused to react in a single stage, in the presence of water and hydrogen at a temperature of from 20° to 300° C. and a pressure of from 1 to 300 bar in a neutral or acidic environment over a hydrogenating catalyst.

In the process of the invention 2 reaction stages are thus carried out in a single process stage, ie a) the reaction of 2,3-dihydrofuran with water to form a mixture of 4-hydroxybutyraldehyde and its isomer 2-hydroxytetrahydrofuran as shown in equation (1)

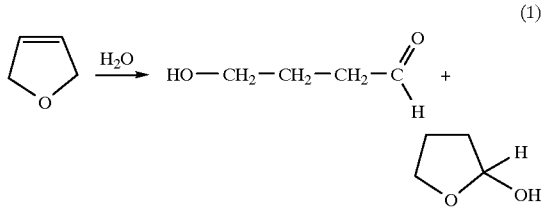

(1)

and b) the catalytic hydrogenation of the mixture obtained as per equation (1) and consisting of 4-hydroxybutyraldehyde and 2-hydroxytetrahydrofuran—both compounds being in equilibrium with each other—to form 1,4-butanediol as shown in equation (2)

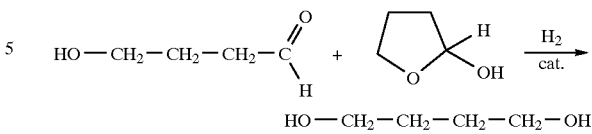

(2)

When carrying out the process of the invention the 2,3-dihydrofuran is generally caused to react with water in a molar ratio of 2,3-dihydrofuran to water of from 1:1 to 1:100, preferably from 1:1 to 1:50, and more preferably from 1:1 to 1:10 and in the presence of hydrogen and a hydrogenating catalyst at a pressure of, in general, from 1 to 300 bar, preferably from 5 to 250 bar, and more preferably from generally 15 to 200 bar and at a temperature of from 20° to 300° C., preferably from 40° to 230° C., and more preferably from 80° to 200° C. to form 1,4-butanediol.

The reaction of the invention is carried out in a neutral or acidic environment, ie at pH's of the aqueous phase which are in the acid or neutral pH range, preferably at pH's in the range of from 2 to 7.5, particularly from 4 to 7.2, and more particularly in the range of from 6 to 7. When use is made of water-insoluble heterogeneous catalysts, operating the process in a neutral or acidic environment means that the catalysts used act non-basically and preferably contain Lewis or Broensted acid centers which influence the course of the reaction in the desired manner, that is to say to effect the formation of predominantly 1,4-butanediol.

Suitable hydrogenation catalysts for use in the process of the invention are generally all catalysts which are suitable for the hydrogenation of carbonyl groups.

It is possible to use hydrogenation catalysts homogeneously dissolved in the reaction medium, as described, for example, in Houben-Weyl, *Methoden der Organischen Chemie*, Vol. IV/1c, pp 45 to 67, Thieme Verlag, Stuttgart 1980 or alternatively heterogeneous hydrogenation catalysts, as described in Houben-Weyl, *Methoden der Organischen Chemie*, Vol. IV/1c, pp 16 to 26. Preferred homogeneous catalysts are, in particular, the complexes of rhodium, ruthenium and cobalt with phosphine or phosphite ligands, the preparation of which is described in eg CA-A 7,276 41, H. Brunner in Hartley: *The chemistry of the metal-carbon bond*; Vol 5, pp 110 to 124, John Wiley & Sons, New York 1989 and Toth et al, *Inorg. Chim. Acta* 42, 153 (1980) and the literature cited therein.

Preferably, however, the process of the invention is carried out using heterogeneous hydrogenation catalysts, ie those hydrogenation catalysts which are substantially insoluble in the reaction medium. Of these hydrogenation catalysts is those are preferred which contain one or more elements from Group Ib, VIIb, and VIIIb of the Periodic Table, in particular copper, rhenium, or ruthenium, or mixtures of these elements.

Other preferred catalysts are those containing at least one element from Group Ib, VIIb, or VIIIb and in addition at least one further element from Groups Ib, Vb, VIb, VIIb, VIIb, IIIa, or IVa of the Periodic Table, which forms a mixture or alloy with the said element or elements from Group Ib, VIIb, or VIIIb. In addition to said elements copper, rhenium and ruthenium, other elements, given by way of example only, are chromium, molybdenum, tungsten, cobalt, rhodium, iridium, nickel, palladium, iron, and/or platinum.

In the process of the invention use may be made of heterogeneous hydrogenation catalysts which consist of metals in activated, finely divided form having a large surface area, for example, Raney copper or rhenium sponge.

There may also be used in the process of the invention, eg, so called precipitation catalysts. Such catalysts can be prepared by precipitating their catalytically active components from their salt solutions, in particular from the solutions of their nitrates and/or acetates, for example, by the addition of solutions of alkali metal and/or alkaline earth metal hydroxide and/or carbonate, said precipitates being, for example, difficultly soluble hydroxides, oxide hydrates, basic salts, or carbonates, followed by drying the precipitates obtained and then converting them by calcination in general at from 300° to 700° C., in particular from 400° to 600° C., to the respective oxides, mixed oxides and/or mixed-valency oxides, which are reduced by treatment with hydrogen or with gases containing hydrogen usually at from 100° to 700° C., in particular at a temperature of from 150° to 400° C., to the respective metals and/or oxidic compounds of a lower oxidation stage and are converted to the desired catalytically active form. Reduction is usually continued until no more water is formed. When preparing precipitation catalysts containing a support material, the precipitation of the catalytically active components can take place in the presence of the respective support material. Alternatively, the catalytically active components can be advantageously precipitated simultaneously with the support material from the respective salt solutions.

It is preferred to operate the process of the invention using hydrogenation catalysts which contain, deposited on a support material, the metals or metal compounds capable of catalyzing the hydrogenation. Apart from the aforementioned precipitation catalysts additionally containing a support material in addition to the catalytically active components, generally those supported catalysts are suitable for the process of the invention in which the components having a catalytically is hydrogenating action have been applied to a support material, eg, by impregnation.

The method used to apply the catalytically active metals to the support is not usually critically important and can be carried out in a number of ways. The catalytically active metals can be applied to these support materials, eg, by impregnation with solutions or suspensions of the salts or oxides of the respective elements, followed by drying and the reduction of the metal compounds to the respective metals or compounds of a lower oxidation stage by means of a reducing agent, preferably with the aid of hydrogen or complex hydrides. Another possible procedure for applying the catalytically active metals to these supports comprises impregnating the supports with solutions of thermally readily decomposable salts, eg, with nitrates or thermally readily decomposable complex compounds, eg with carbonyl or hydride complexes of the catalytically active metals, and heating the resulting impregnated supports to effect thermal decomposition of the adsorbed metal compounds, at temperatures of from 300° to 600° C. This thermal decomposition is preferably carried out under a blanket of protective gas. Suitable protective gases are, eg, nitrogen, carbon dioxide, hydrogen, or the noble gases. Furthermore, th e catalytically active metals can be deposited on the catalyst support by vapor deposition or by flame spraying.

The content of catalytically active metals in these supported catalysts of the invention is theoretically not critically important for the success of the process. It will be apparent to the person skilled in the art that higher contents of catalytically active metals in these supported catalysts lead to higher space-time yields than do lower contents. However, supported catalysts are generally used in which the content of catalytically active metals is from 0.1 to 80 wt %, preferably from 0.5 to 30 wt %, based on the total catalyst. Since these contents data refer to the total catalyst, including the support material, and since different support materials have very different specific gravities and specific surface areas, the actual values may be above or below those stated without this being detrimental to the results achieved by the process of the invention. Of course, a number of catalytically active metals can be applied to the respective support material if desired. Furthermore, the catalytically active metals can be applied to the support by the methods described in DE-A 2,519,817, EP-A 1,477,219, and EP-A 285,420, for example. In the catalysts described in the aforementioned references, the catalytically active metals are present in the form of alloys produced by thermal treatment and/or reduction of salts or complexes of the aforementioned metals after said salts or complexes have been deposited o n a support, eg, by impregnation.

The activation of the precipitation catalysts and the supported catalysts can be is effected, if desired, in situ in the reaction mixture by the hydrogen present therein. However, these catalysts are preferably activated separately prior to their use.

The support materials used are generally the oxides of aluminum and titanium, zirconium dioxide, silicon dioxide, kieselguhr, silica gel, argillaceous earths, eg, montmorillonites, silicates, such as magnesium or aluminum silicates, zeolites, such as ZSM-5 or ZSM-10 zeolites, and activated charcoal. Preferred support materials are aluminum oxides, titanium dioxides, zirconium dioxide, and activated charcoal. Of course, mixtures of various support materials can, if desired, serve as supports for catalysts that can be used in the process of the invention.

The following catalysts may be mentioned as examples of heterogeneous catalysts which can be used in the process of the invention:

Manganese on activated charcoal, rhenium on activated charcoal, rhenium on silicon dioxide, rhenium/tin on activated charcoal, rhenium/palladium on activated charcoal, rhenium/copper on activated charcoal, rhenium/nickel on activated charcoal, copper on activated charcoal, copper on silicon dioxide, copper on aluminum oxide, copper chromite, and barium copper chromite.

There can be added to the catalysts Lewis and/or Broensted acid components, such as zeolites, aluminum or silicon oxides, phosphoric acid or sulfuric acid. They are generally added in amounts of from 0.01 to 5 wt %, preferably from 0.05 to 0.5 wt % and in particular of from 0.1 to 0.4 wt %, based on the weight of the catalyst used.

It is particularly preferred to carry out the process of the invention using hydrogenation catalysts which contain Broensted and/or Lewis acid centers. When use is made of such catalysts, it is generally unnecessary to make further addition of a Broensted or Lewis acid to the reaction mixture.

Examples of useful homogeneous catalysts containing Broensted acid centers are transition metal complexes of metals of Group VIIIb, particularly rhodium, ruthenium, and cobalt complexes with phosphine or phosphate ligands, which carry functional Broensted acid groups such as carboxyl groups, sulfonic acid groups, and/or phosphonic acid groups, as substituents, for example complexes of the cited transition metals with triphenylphosphine-p-sulfonic acid ligands. Such ligands can be prepared eg by the process described in *Angew. Chem.* 105, 1097 (1993).

Particularly advantageous results can be achieved in the process of the invention by using heterogeneous catalysts containing Broensted or Lewis acid centers. For example, the catalytically active metals themselves can act as Broensted or Lewis acid centers, if they are not completely reduced to the respective metals during activation of the catalyst with hydrogen or hydrogenous gases. This applies, eg, to the rhenium and chromite-containing catalysts such as rhenium black and copper chromite. In rhenium black, rhenium is present as a mixture of rhenium metal with rhenium compounds in higher stages of oxidation, in which case the latter can cause effects like Lewis or Broensted acids. Furthermore, such Lewis or Broensted acid centers can be introduced into the catalyst via the support material used. As examples of suitable support materials containing Lewis or Broensted acid centers there may be mentioned the aluminum oxides, titanium dioxides, zirconium dioxide, silicon dioxide, the silicates, argillaceous earths, zeolites, and activated charcoal.

Thus it is particularly preferred to operate the process of the invention using, as hydrogenation catalysts, supported catalysts containing at least one element from Groups Ib, VIIb, or VIIIb of the Periodic Table, in particular copper, rhenium and/or ruthenium, or at least one element from Groups Ib, VIIb, or VIIIb and in addition at least one further element from Groups Ib, Vb, VIb, VIIb, VIIIb, IIIa, or IVa of the Periodic Table, which element forms a mixture or alloy with the said element(s) of Groups Ib, VIIb, or VIIIb, deposited on a support material which is effective as a Broensted or Lewis acid. Particularly advantageous catalysts are, eg, rhenium on activated charcoal, rhenium on zirconium dioxide, rhenium on titanium dioxide, rhenium on silicon dioxide, copper on activated charcoal, copper on silicon dioxide, and ruthenium on activated charcoal.

The process of the invention can be carried out both continuously and batchwise.

To effect continuous operation, use can advantageously be made of tubular reactors, for example, in which the catalyst is advantageously arranged in the form of a fixed bed, over which the reaction mixture can be passed in the upward-flow mode or downward-flow mode. When the process is carried out batchwise, simple stirred reactors or, advantageously, recycle reactors can be used. When use is made of recycle reactors, the catalyst is advantageously in the form of a fixed bed. When there is incomplete conversion of the starting material, this can advantageously be recycled to the reaction either following the separation, by distillation, of the desired products or as a partial stream which includes the other reaction products. This may be particularly advantageous when the process is carried out continuously. Higher yields are generally obtained when the reaction is carried out continuously to produce 1,4-butanediol than when the reaction is carried out batchwise using the same catalyst.

The process of the invention can be advantageously carried out in the presence of a solvent inert unter the reaction conditions, for example, a water-soluble ether, such as tetrahydrofuran, dioxane, or dimethoxymethane. Alternatively and advantageously, alcohols, particularly the end product 1,4-butanediol, can be used as solvents.

The effluent obtained is generally a mixture mainly composed of excess water and 1,4-butanediol. By-products which may be present in the effluent in minor quantities are, for example, γ-butyrolactone, tetrahydrofuran, and n-butanol. The effluent can be worked up by conventional methods, eg, by distillation, in order to isolate 1,4-butanediol and any by-products γ-butyrolactone, tetrahydrofuran, or n-butanol present in the effluent. In this process any unconverted 2,3-dihydrofuran and any solvent used can be recovered and recycled to the reaction. In the case of incomplete conversion of the 2,3-dihydrofuran, the effluent can be post-treated, before it is worked up, in a follow-up reactor to achieve quantitative conversion.

The 2,3-dihydrofuran required as starting material can be obtained, eg, using the process described in U.S. Pat. No. 3,828,077 by partial hydrogenation of furan.

1,4-butanediol is prepared world-wide in vast quantities and serves as a diol component for the preparation of, inter alia, polyesters, polyurethanes, and epoxide resins.

EXAMPLES

The yields given in the following examples are stated in molar percentages and were determined by gas chromatography.

Example 1

In a metal autoclave having a capacity of 50 mL and equipped with a stirrer there were placed 2 g of a rhenium on activated charcoal catalyst which had been activated at 300° C. in a stream of hydrogen and which had a rhenium content of 6 wt %, calculated as Re and based on the weight of the catalyst, 5 g of 2,3-dihydrofuran, and 15 g of water. Hydrogen was then forced in to establish a pressure of 50 bar and the autoclave was heated to 170° C. After a period of 1 h, the autoclave was cooled an d depressurized. The effluent had the following composition: 77 mol % of 1,4-butanediol, 20 mol % of γ-butyrolactone, 1.3 mol % of tetrahydrofuran, 1.3 mol % of n-butanol, and 0.3 mol % of n-propanol.

Example 2

In a manner similar to that described in Example 1, 5 g of 2,3-dihydrofuran and 5 g of water were caused to react for two hours over 2 g of a copper on activated charcoal catalyst (copper content 10 wt %, calculated as Cu and based on the total weight of the catalyst; prepared by impregantion of the activated charcoal with the appropriate amount of a copper ammoniate solution, followed by drying at 120° C. and activation for 2 hours in a stream of hydrogen at 300° C.). The effluent had the following composition: 95 mol % of 1,4-butanediol, 4 mol % of γ-butyrolactone, and 0.8 mol % of tetrahydrofuran. The remainder consisted mainly of the acetal of 2-hydroxytetrahydrofuran and 1,4-butanediol.

Example 3

25 mL of the catalyst described in Example 1 were positioned in a tubular reactor having a capacity of 25 mL. 10 g/h of 2,3-dihydrofuran and 5 g/h of water were then passed to the top of the reactor via two separate feed lines. The hydrogen pressure in the reactor was 120 bar, and the temperature was 166° C. The off-gas rate was 50 L/h. In the effluent there were present, at 97% conversion, 80 mol % of 1,4-butanediol, 1.6 mol % of tetrahydrofuran, 8.3 mol % of γ-butyrolactone, and 1.3 mol % of n-butanol. The remainder consisted of the acetal of 2-hydroxytetrahydrofuran and 1,4-butanediol.

Effluent collected over a period of 8 h was passed, on completion of the test run, again over the same catalyst under the same reaction conditions (one feed line 20 g/h). At a quantitative 2,3-dihydrofuran conversion, there were obtained the following yields: 92 mol % of 1,4-butanediol, 1.9 mol % of tetrahydrofuran, 4.1 mol % γ-butyrolactone, and 2 mol % of n-butanol.

We claim:

1. A process for the preparation of 1,4-butanediol, which consists essentially of reacting 2,3-dihydrofuran over a hydrogenating catalyst, in a single stage, in the presence of water and hydrogenation at a temperature of from 20° to 300° C. and a pressure of from 1 to 300 bar in a neutral or acidic environment.

2. A process as defined in claim 1, wherein a heterogeneous hydrogenating catalyst is used.

3. A process as defined in claim 1, wherein a hydrogenating catalyst is used which contains at least one element from Group Ib or VIIb or VIIIb of the Periodic Table or a mixture of said elements.

4. A process as defined in claim 1, wherein a hydrogenating catalyst is used of which the catalytically active component has been applied to a support.

5. A process as defined in claim 1, wherein a hydrogenating catalyst is used which contains one or more components effective as Broensted or Lewis acids.

6. A process as defined in claim 1, wherein a hydrogenating catalyst is used which contains rhenium.

7. A process as defined in claim 1, wherein a hydrogenating catalyst is used which contains copper.

8. A process as defined in claim 1, wherein a hydrogenating catalyst is used which contains ruthenium.

9. A process as defined in claim 1, wherein the catalyst contains at least one element from Group Ib, VIIb or VIIIb and in addition at least one further element from Group Ib, Vb, VIb, VIIb, VIIIb, IIIa, and IVa of the Periodic Table which forms a mixture or an alloy with said element or elements from Group Ib or VIIb or VIIIb.

10. A process as defined in claim 1, wherein a hydrogenating catalyst is used, the catalytically active component of which has been applied to a support material containing aluminum oxide, argillaceous earth, silicon dioxide, zirconium dioxide, titanium dioxide, a zeolite, and/or activated charcoal.

11. A process as defined in claim 1, wherein a homogeneous hydrogenating catalyst is used which contains an element from Group VIIIb of the Periodic Table.

* * * * *